United States Patent
Synowicki et al.

(10) Patent No.: US 10,466,171 B1
(45) Date of Patent: Nov. 5, 2019

(54) METHOD OF DETERMINING REFRACTIVE INDICES AND SURFACE PROPERTIES OF PRISM SHAPED MATERIAL

(71) Applicant: J.A. WOOLLAM CO., INC., Lincoln, NE (US)

(72) Inventors: Ronald A. Synowicki, Lincoln, NE (US); Joel J. Mohrmann, Lincoln, NE (US)

(73) Assignee: J.A. WOOLLAM CO., INC., Lincoln, NE (US)

( * ) Notice: Subject to any disclaimer, the term of this patent is extended or adjusted under 35 U.S.C. 154(b) by 0 days.

(21) Appl. No.: 16/501,681

(22) Filed: May 22, 2019

Related U.S. Application Data

(63) Continuation of application No. 15/530,775, filed on Feb. 27, 2017, now Pat. No. 10,309,897.

(60) Provisional application No. 62/389,559, filed on Mar. 3, 2016.

(51) Int. Cl.
*G01J 4/00* (2006.01)
*G01N 21/41* (2006.01)
*G01N 21/21* (2006.01)

(52) U.S. Cl.
CPC ....... *G01N 21/4133* (2013.01); *G01N 21/211* (2013.01); *G01N 2021/214* (2013.01)

(58) Field of Classification Search
CPC ............. G01N 21/211; G01N 21/4133; G01N 2021/214
USPC .................................. 356/134, 130, 72, 364
See application file for complete search history.

(56) References Cited

U.S. PATENT DOCUMENTS

| | | | | |
|---|---|---|---|---|
| 7,280,194 B1 * | 10/2007 | Herzinger | .......... | G01N 21/4133 356/128 |
| 8,692,985 B1 * | 4/2014 | Synowicki | ............. | G01N 21/43 356/128 |
| 2017/0254748 A1 * | 9/2017 | Synowicki | ......... | G01N 21/4133 |

* cited by examiner

*Primary Examiner* — Sunghee Y Gray
(74) *Attorney, Agent, or Firm* — James D. Welch

(57) ABSTRACT

Methodology of characterizing surface properties and determining refractive index and extinction coefficient of a prism shaped material, including simultaneously for a multiplicity of wavelengths, using an easy to practice technique.

11 Claims, 7 Drawing Sheets

METHOD OF DETERMINING REFRACTIVE INDICES AND SURFACE PROPERTIES OF PRISM SHAPED MATERIAL

This Application is a Continuation of Ser. No. 15/530,775, and Claims Benefit of 62/389,559.

TECHNICAL FIELD

The present invention relates to methodology for determining refractive index and extinction coefficients of a material, and more particularly to a method of quickly doing so while also characterizing surface properties for a multiplicity of wavelengths utilizing, for instance, a (θ)-(θ) sample investigation system, for a material that is prism shaped and positioned in a system that uses electromagnetic radiation to investigate samples, having source and detector side arms that rotate about a common axis.

BACKGROUND

A Patent to Synowicki et al., U.S. Pat. No. 8,692,985 is disclosed as particularly relevant to the present invention. It, however, does not disclose ellipsometric sensitivity being mostly to surface properties of a prism.

Another Patent to Herzinger et al. U.S. Pat. No. 7,280,194 is disclosed as it describes methodology for determining Refractive Indicies of solid and fluid materials by placing a prism shaped material on a stage in a (θ)-2(θ) goniometer system, that rotates about an axis. This geometry makes the method thereof difficult to practice in a typical dual arm ellipsometer or the like system, in which the arms secure a source and a detector respectively, and rotate about a horizontally oriented axis to enable projecting a beam of electromagnetic radiation onto a sample on a centrally located stage. The present invention provides an approach for arriving at a similar result to that provided by Herzinger et al. 194, using an alternative sample investigation system arrangement.

In the context of the present invention, the method of determining the refractive index of a prism shaped material in U.S. Pat. No. 7,280,194, can be generally described as comprising the steps of:
  a) providing a system comprising:
    a1) a stage for supporting said prism shaped material;
    a2) a fixed position source of a beam of electromagnetic radiation mounted on an source side of said stage for supporting said prism shaped material, and a detector of a beam of electromagnetic radiation mounted to a support arm on a: detector side of said stage for supporting a prism shaped material; the positioning of said source of a beam of electromagnetic radiation defining an input angle of incidence to a source side of a prism shaped material when it is positioned on said stage, such that a beam of electromagnetic radiation from said source can be directed to enter the source side of said prism shaped material, be refracted thereby, pass through said prism shaped material and exit from said detector side of said prism shaped material at a refracted exit angle to said detector side of said prism shaped material, and then proceeds toward and enters said detector of beam of electromagnetic radiation;
    a3) a means for rotating the detector side support arm to which said detector is attached, and a means for rotating said stage for supporting said prism shaped material, each through a range of angles.

Said method then further comprises:
  b) mounting a prism shaped material to said stage, said prism shaped material having converging source and detector sides that form an apex angle "A" where they intersect;
  c) while causing said fixed position source of a beam of electromagnetic radiation to provide a beam of electromagnetic radiation directed toward the source side of said prism shaped material at a fixed angle of incidence to the source side thereof, rotating said stage for supporting said prism shaped material and rotating said support arm on said detector side of said prism shaped material to which said detector is attached to selected positions, and monitoring the intensity of the beam entering said detector as a result.
And finally,
  d) while monitoring intensity at the detector to enable determining the minimum deviation condition angle, identify the optimum rotation angles of said stage for supporting said prism shaped material and said support arm on said detector side of said prism shaped material to which said detector is attached, repeating step c) for multiplicity of rotations of said stage for supporting said prism shaped material and said support arm on said detector side of said prism shaped material to which said detector is attached until optimum angles of rotations for both the stage for supporting said prism shaped material and support arm on said detector side of said prism shaped material to which said detector is attached where the minimum deviation condition is achieved, (ie. where the intensity is maximum), and identifying the rotation angle of the support arm on said detector side of said prism shaped material to which said detector is attached as the optimum angle;
  e) for the optimum angle determined in step d) applying the following formula:

$$n2 = \frac{(\sin(A + \theta min)/2)}{\sin(A/2)} n1$$

to determine n2.

Note, n1 and n2 are the refractive indicies of the ambient environment surrounding said prism shaped material, and of said prism shaped material, respectively.

It is noted that this approach utilizes a sample monitoring system in which, for each degree (θ) a beam of electromagnetic radiation from the source is changed to provide an angle of incidence to the sample, the detector angle is changed (2θ). That is, it utilizes a (θ)-(2θ) goniometer system. When the angle of incidence is (θ), the detector catches the beam at (2θ). This involves the detector arm angle being moved as a slave to the source arm angle and then locked in place. The present invention, it will be presented later in this specification, provides for each of the source and detector arms to be moved equal amounts in a (θ)-(θ) system arrangement, rather than utilize a (θ)-(2θ) system arrangement.

Said method involves investigating a solid prism shaped material, or can have an empty volume in said prism shaped material into which is caused to be present a liquid, the optical constants of which are desired to be determined.

Said method can involves using a source of electromagnetic radiation which is spectroscopic and wherein said method is repeated a plurality of times, for a plurality of wavelengths, to determine refractive index at each thereof.

Said method typically involves application of (θ)-(2θ) means for adjusting each of the source side and detector sides support arms through equal angles, by a mechanism that adjusts each of the source and detector side support arms by automatic simultaneous adjustment.

Even in view of the foregoing, need remains for an easy to practice method of characterizing surface properties of a prism, sequentially, or simultaneously with determining refractive indicies of a prism shaped material. This is especially the case when a spectroscopic beam of electromagnetic radiation is used and refractive indicies are to be quickly determined for a multiplicity of wavelengths in a single sweep of source and detector angles-of-entry and exit from the prism shaped material.

DISCLOSURE OF THE INVENTION

Where one wavelength in a beam of electromagnetic radiation is to be investigated at a time, the present invention is a method of determining the refractive index of a prism shaped material, comprising the steps of:
  a) providing a system comprising:
    a1) a stage for supporting said prism shaped material,
    a2) a source of a beam of electromagnetic radiation:
      mounted directly on a rotatable support arm on a source side of said prism shaped material; or
      mounted other than on a rotatable support arm on a source side of said prism shaped material and also providing a beam directing beam director attached to said support arm on a source side of said prism shaped material.
Positioning a detector of a beam of electromagnetic radiation:
  mounted directly on a separate rotatable support arm on a detector side of said prism shaped material, or
  mounted other than on a rotatable support arm on a detector side of said prism shaped material and also providing a beam directing beam director attached to said rotatable support arm on a detector side of said prism shaped material;
each of said sample and detector side rotatable supports being rotatable about a common axis so as to enable directing a beam of electromagnetic radiation provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward and enters said detector of beam of electromagnetic radiation.
Said method also comprises providing:
  a3) means for adjusting each of the source side and detector sides rotatable support arms through equal angles by rotation about said common axis; and
  a4) a computer.
The method then continues with:
  b) mounting a prism shaped material to said stage, said prism shaped material having converging source and detector sides that form an apex angle "A" where they intersect;
  c) while causing said source of a beam of electromagnetic radiation to provide a beam of electromagnetic radiation, rotating said rotatable support arm on said source side of said prism shaped material clockwise or counterclockwise some number of degrees to direct a beam of electromagnetic radiation toward the source side of said prism shaped material at an angle of incidence to said source side thereof, and rotating said separate rotatable support arm on said detector side of said prism shaped material counterclockwise or clockwise respectively, to the same magnitude number of degrees as was the rotatable support arm to which the source is attached and monitoring the intensity of the beam entering said detector as a result;
  d) repeating step c) for multiplicity of additional input beam angles of incidence and monitoring the intensity of the beam entering said detector as a result for each said angle to determine the optimum angle of incidence of said electromagnetic beam with respect to said source side of said prism shaped material at which the detector indicates a maximum intensity; and
  e) for the optimum maximum intensity angle of incidence determined in step d), in said computer, applying the following formula:

$$n2 = \frac{(\sin((A + (180 - 2(\theta) \text{ optimum angle}))/2))}{\sin(A/2)} n1$$

to determine n2,
where n1 and n2 are the refractive indicies of the ambient environment surrounding said prism shaped material, and of said prism shaped material, respectively.
The present invention method is characterized by:
  f) said method further comprising adapting the source provided in step a2), or providing a different source of electromagnetic radiation to serve as an ellipsometer system source of a beam of electromagnetic radiation, then causing a beam provided thereby to pass through a polarization state generator, follow a substantially similar path as did the source of a beam of electromagnetic radiation provided in step a2) through said prism material oriented as in step e), pass through a polarization state analyzer and enter the same detector as also provided in step a2), or a different detector of electromagnetic radiation, which same or different detector serves as said ellipsometer system detector, followed by acquiring ellipsometric data from said detector and applying it to characterize surface properties of said prism.

It is to be appreciated that the source of electromagnetic radiation can be spectroscopic and said method can be repeated a plurality of times, for a plurality of wavelengths, to determine refractive index at each thereof.

A MODIFIED METHOD of simultaneously determining the refractive index of a prism shaped material for a multiplicity of wavelengths, comprises the steps of:
  a) providing a system comprising:
    a1) a stage for supporting said prism shaped material,
    a2) a source of a spectroscopic beam of electromagnetic radiation:
      mounted directly to a rotatable support arm on a source side of said prism shaped material, or
      mounted other than to said rotatable support arm and provides a spectroscopic beam via a beam director attached to a support arm on a source side of said prism shaped material;
  and a wavelength disperser and multi-element detector of different wavelengths in a beam of electromagnetic radiation mounted:

mounted directly to a separate rotatable support arm on a detector side of said prism shaped material, or mounted other than to said rotatable support arm and directs a spectroscopic beam via a beam director mounted to a support arm on a detector side of said prism shaped material;

said source side and detector side rotatable support arms each being rotatable about a common axis so as to enable directing a beam of electromagnetic radiation, provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward said wavelength disperser where it is dispersed into separate wavelengths which enter said detector of spectroscopic beam of electromagnetic radiation.

Said method also comprises providing:

a3) means for adjusting each of the source side and detector sides rotatable support arms through equal angles by rotation about said common axis; and a4) a computer.

Said method continues with:

b) mounting a prism shaped material to said stage, said prism shaped material having converging source and detector sides that form an apex angle "A" where they intersect;

c) while causing said source of a beam of electromagnetic radiation to produce a spectroscopic beam of electromagnetic radiation, rotating said rotatable support arm on said source side of said prism shaped material counterclockwise or clockwise through a range of angles to direct a beam of electromagnetic radiation toward the source side of said prism shaped material at an angle of incidence to said source side thereof, and rotating said separate rotatable support arm on said detector side of said prism shaped material clockwise or counterclockwise, respectively, through the same range of angles as was the rotatable support arm to which the source is attached, and simultaneously monitoring the intensity of a multiplicity of dispersed wavelengths in said beam entering different detecting elements of said detector as a result;

d) monitoring the intensity of each of said multiplicity of dispersed wavelengths in the beam entering the multiple elements of said detector as a result by so doing determining the optimum angle of incidence of each wavelength in said electromagnetic beam with respect to said source side of said prism shaped material at which the detector indicates a maximum intensity; and e) for the optimum maximum intensity angle of incidence determined in step d), in said computer, applying the following formula:

$$n2 = \frac{(\sin((A + (180 - 2(\theta) \text{ optimum angle}))/2))}{\sin(A/2)} n1$$

to determine n2, where n1 and n2 are the refractive indicies of the ambient environment surrounding said prism shaped material, and of said prism shaped material, respectively, where n2 is wavelength dependent.

Said method is characterized by:

f) said method further comprising adapting the source provided in step a2), or providing a different source of electromagnetic radiation to serve as an ellipsometer system source of a beam of electromagnetic radiation, then causing a beam provided thereby to pass through a polarization state generator, follow a substantially similar path as did the source of a beam of electromagnetic radiation provided in step a2) through said prism material oriented as in step e), pass through a polarization state analyzer and enter the same detector as also provided in step a2), or a different detector of electromagnetic radiation, which same or different detector serves as said ellipsometer system detector, followed by acquiring ellipsometric data from said detector and applying it to characterize surface properties of said prism.

In both method embodiments the source of said, for instance, spectroscopic beam of electromagnetic radiation can be directly attached to the said rotatable support arm on said source side of said prism shaped material, and the beam diffractor and detector of electromagnetic radiation exiting said prism shaped material can be directly attached to said rotatable support arm on said detector side of said prism shaped material.

In both method embodiments the source of said spectroscopic beam of electromagnetic radiation can provide a beam that is directed to the prism shaped material by a beam director that is attached to the said support arm on said source side of said prism shaped material, and/or the beam of electromagnetic radiation exiting said prism shaped material can be directed to the beam diffractor and detector by a beam director that is attached to said support arm on said detector side of said prism shaped material.

In both method embodiments the step of providing said means for adjusting each of the source side and detector sides support arms through equal angles, can involve providing a mechanism that adjusts each of the source and detector side rotatable support arms independently.

In both method embodiments the step of providing said means for adjusting each of the source side and detector sides rotatable support arms through equal angles, can involve providing a theta ($\theta$)-theta ($\theta$) mechanism wherein adjusting the source side rotatable support arm, automatically results in said detector side rotatable support arm being adjusted.

In both method embodiments the prism shaped material can have an empty volume therein and into which is caused to be present a liquid, the optical constants of which are to be determined.

In both method embodiments said method can further comprise determining the extinction coefficient of said prism shaped material, by:

g) changing the position of said stage so that the electromagnetic beam passing therethrough passes through a different length of said prism shaped material, and monitoring the output of said detector of a beam of electromagnetic radiation to provide the intensity exiting said prism shaped material; and h) applying said intensity value obtained in step g, and the intensity value previously obtained in step c, and relating them to path lengths of said beam as it passes through said prism shaped material, to determine the extinction coefficient.

Note: Practice of steps g) and h) will typically involve changing of position of the stage by moving it, for instance, up or down where the stage is oriented horizontally. This will cause the beam to transverse a different length of prism shaped material as it passes therethrough.

In both method embodiments the common axis about which the rotatable source side support and detector side support arms rotate can be oriented substantially horizontally, or substantially vertically in lab coordinates.

In both embodiments the prism shaped material can be of a known refractive index, and its measured value used to calibrate the system so that it reads accurately as well as repeatable.

In both method embodiments, the steps can be carried out under control of a computer and/or the method can include storing at least some output provided by the detector in non-transitory machine readable media, and analyzing at least some output provided by the detector.

In both method embodiments, it is noted that the stage for supporting said prism shaped material need not be rotatable, as is required in ($\theta$)-($2\theta$) system described in that Background Section of this Specification, but it is able to be moved, for instance, up and down where the stage is mounted horizontally, in laboratory coordinates. In fact, the stage can be fixed in place as regards rotation in the present invention.

In both method embodiments said means for adjusting each of the source side and detector sides rotatable support arms through equal angles, can involve providing a mechanism that adjusts each of the source and detector side rotatable support arms independently, or involves providing a theta ($\theta$)-theta ($\theta$) mechanism wherein adjusting the source side rotatable support arm automatically results in said detector side rotatable support arm being adjusted.

Also, in both method embodiments, where a prism shaped material is of a known refractive index its measured value can be used to calibrate the system so that it reads accurately, as well as repeatedly. This would involve adjusting measurement system parameters so that the measured reading is what is expected for said known sample.

Further, in both method embodiments the source of a spectroscopic beam of electromagnetic radiation can be directly attached to the said rotatable support arm on said source side of said prism shaped material, and the beam diffractor and detector of electromagnetic radiation exiting said prism shaped material can be directly attached to said rotatable support arm on said detector side of said prism shaped material, or beam directors can be attached to the source and detector side arms and the actual source and detector of electromagnetic radiation be located at another location.

The invention will be better understood by reference to the Detailed Description Section of this Specification, and the accompanying Drawings.

DETAILED DESCRIPTION

Figure 1:
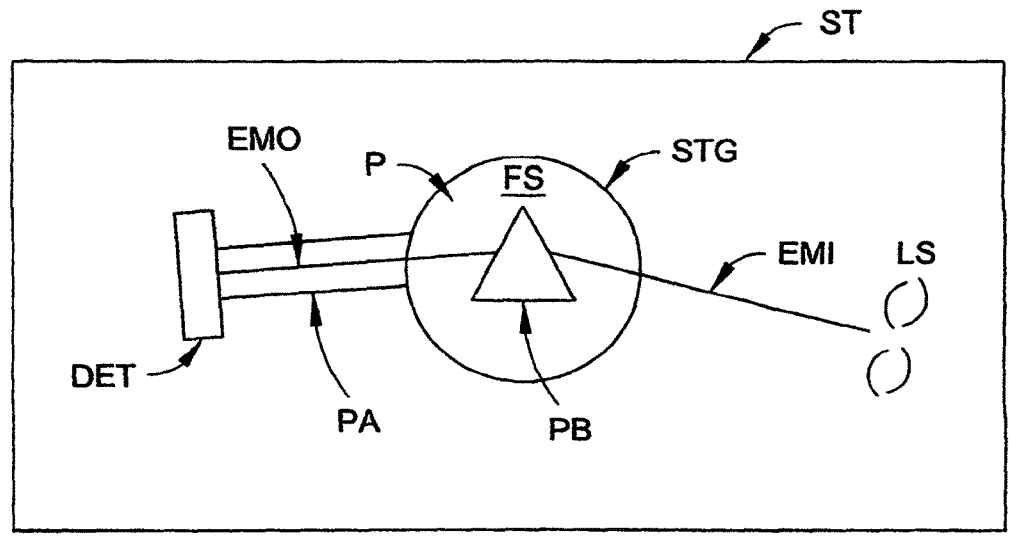
FIGS. 1 and 2 are FIGS. 1 and 2 in Herzinger U.S. Pat. No. 7,280,194.
Figure 2:
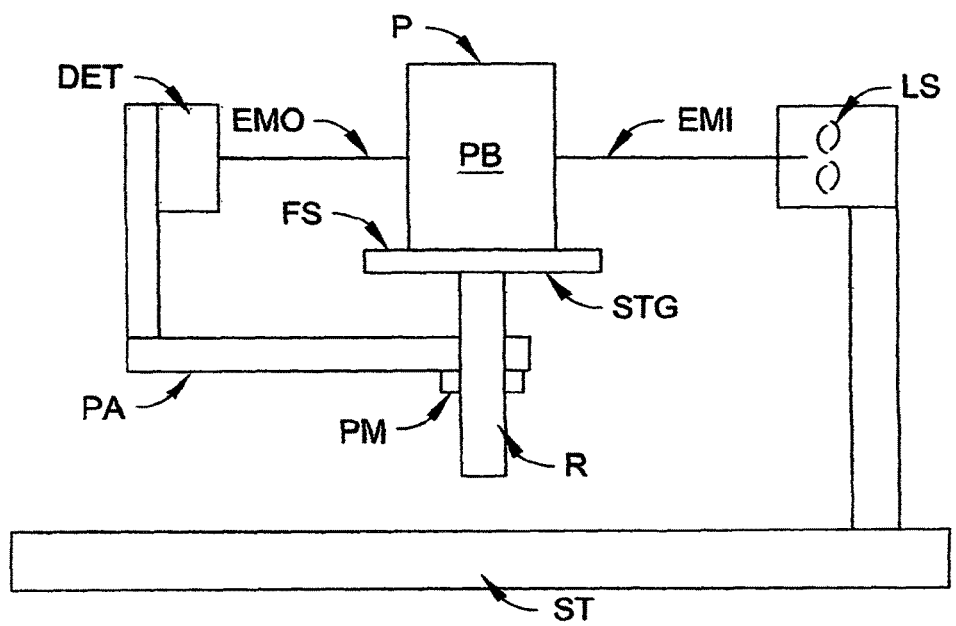

Turning now to the Drawings, FIGS. 1 and 2 duplicate FIGS. 1 and 2 in the Herzinger 194 Patent. The Stage (FS) is oriented so that its sample supporting surface (FS) faces upward, and so that it can be rotated about a vertical axis, and the Source (LS) of electromagnetic radiation, and Detector (DET) thereof move in a demonstrative horizontally oriented plane. This works well, but is not consistent with the geometry of many typical ellipsometer and other systems that comprise a Theta ($\theta$)-Theta ($\theta$) goniometer.

Figure 3:
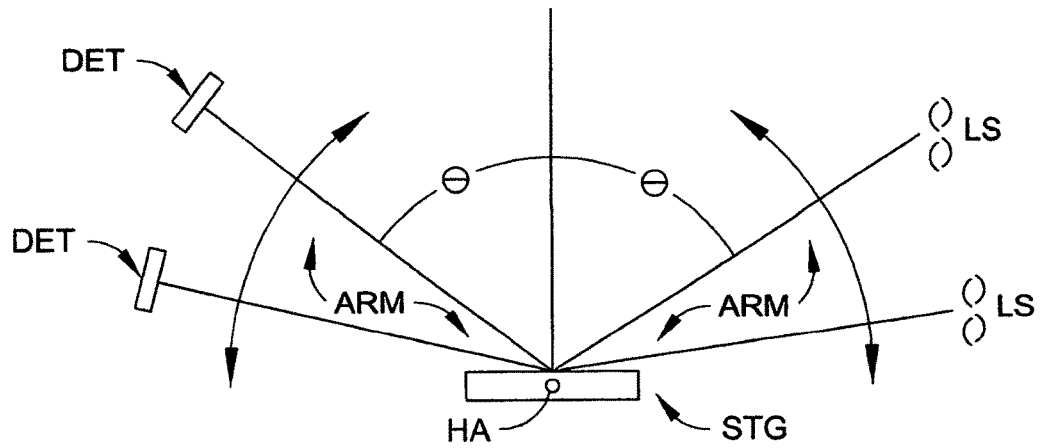
FIG. 3 shows a typical ellipsometer system configuration with source and detector rotatable arms mounted in a ($\theta$)-($\theta$) configuration.

FIG. 3 shows a more typical goniometer system configuration in an ellipsometer or other sample investigation system that utilizes electromagnetic beams. Note that the sample supporting Stage (STG) surface (FS) is shown facing upward for demonstrative purposes, and also that the Source (LS) of electromagnetic radiation and Detector (DET) thereof move in a vertically oriented plane in what can be termed a rotational motion that controls the angles ($\theta$) of incidence of the electromagnetic radiation input beam (EMI) from said Source (LS) onto said Stage (STG) and its reflection angle toward the Detector (DET). Said Source (LS) and Detector (DET) are shown mounted to Arms (ARM) to enable said motion. It is noted that as shown, the stage (STG) can be provided the capability of moving up and down, and such capability is applied in the present invention to enable determination of prism material extinction coefficient. Further, it is to be understood that the system could be arranged to allow stage (STG) rotations about a demonstrative horizontal axis, rather than a vertically oriented axis, but this capability is generally not utilized in the present invention methodology where the stage rotationally fixed. The FIG. 3 configuration is consistent with many conventional ellipsometer, and other systems that utilize electromagnetic beams to investigate samples, such as those manufactured by the J.A. Woollam CO. In use the Stage (STG) can be fixed in position and the Arms (ARM) rotated in a demonstrative vertically oriented plane about a demonstrative horizontally oriented axis, or the Source (LS) can be fixed in position and the Arm (ARM) to which the Detector (DET) is attached, and the Stage (STG) rotated about demonstrative horizontally oriented axes. FIG. 3 demonstrates a ($\theta$)-($\theta$) goniometer scenario. FIG. 3 is be interpreted as demonstrating any means, manual, motorized etc. for moving said arms (ARM) on both Source (LS) and Detector (DET) sides, and vertically.

Figure 4:
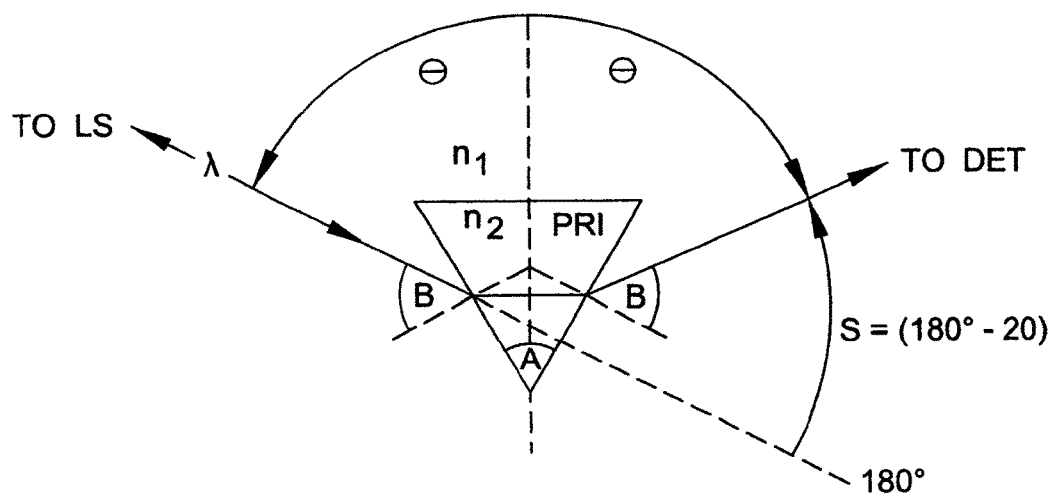
FIG. 4 shows that where a Prism Shaped Material (PRI) is placed on a stage (STG) the ($\theta$)-($\theta$) goniometer scenario is altered in that the Theta ($\theta$) angles of incidence and exit are changed by said Prism Shaped Material (PRI).

FIG. 4 shows that where a Prism Shaped Material (PRI) is placed on a stage (STG) the (θ)-(θ) goniometer scenario is altered in that the Theta (θ) angles of incidence and reflection are changed by said Prism Shaped Material (PRI). However, where the angles (β) are made to be equal by rotation of the Source (LS) and Detector locations in a vertically oriented plane, what is termed the "Minimum Deviation" condition is achieved. At that condition FIG. 4 indicates that the Refractive Index ($n_2$) can be calculated.

Figure 5:
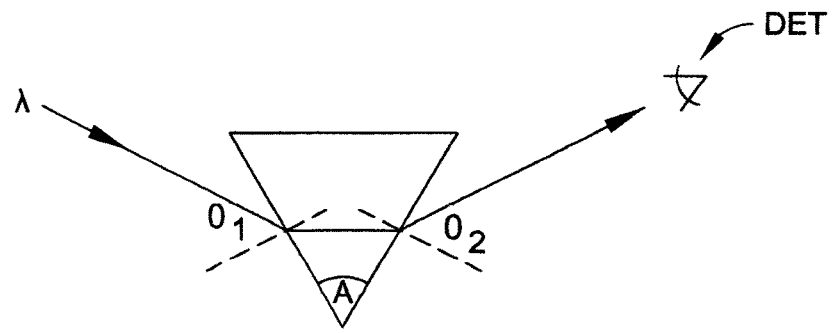
FIGS. 5 & 6 indicates a traditional ($\theta$)-2($\theta$) goniometer configuration that can be applied to determine the refractive index utilizing a Stage (STG) and a Detector (DET) that can each be rotated. Note, (A) and ($\theta$) angles are measured in degrees.
Figure 6:
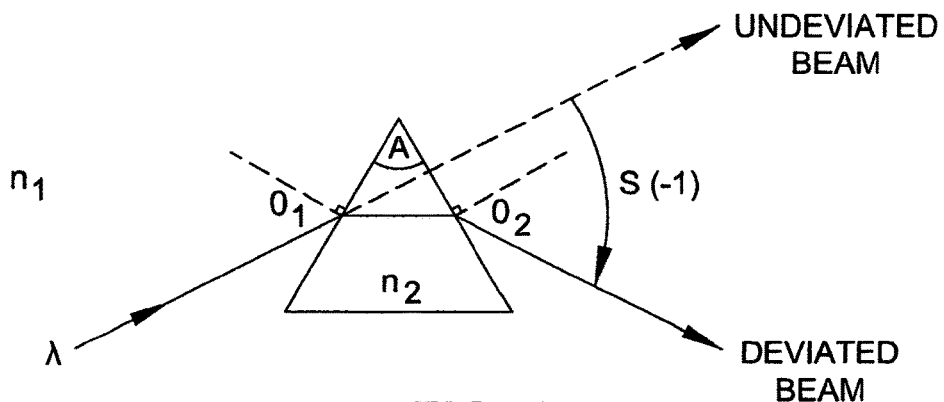

FIGS. 5 and 6 indicate a traditional (θ)-2(θ) approach to achieving a similar result wherein the Stage (STG) and Detector (DET) are rotated in a Vertically oriented plane. FIGS. 1, 2, 5 and 6 are included to provide contrast to the (θ)-(θ) system utilized in the present invention methodology, insight to which is provided in FIGS. 3, 4 and 7.

Figure 7:
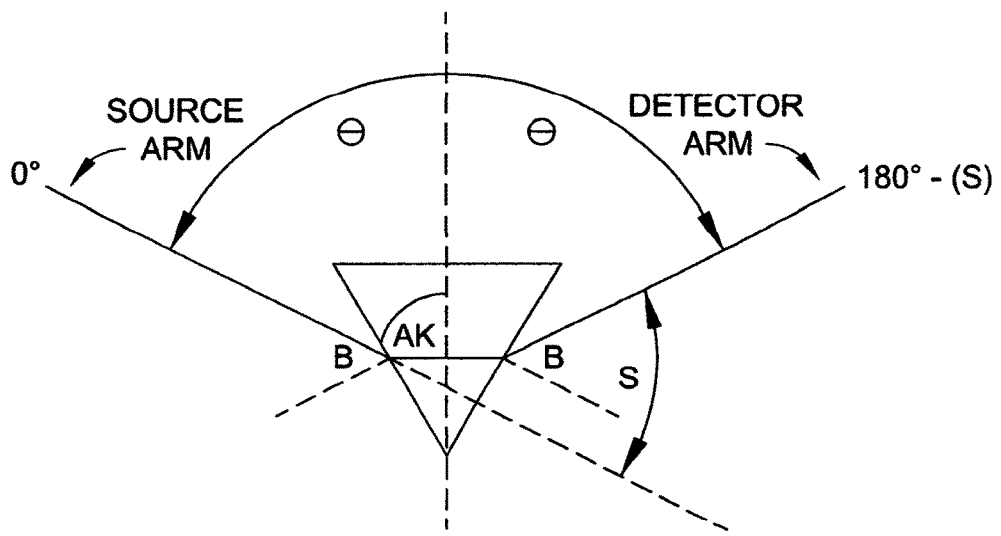
FIG. 7 shows a goniometer system for practicing the present invention Minimum Deviation ($\theta$)-($\theta$) method that enables an intensity measurement approach to determining the Refractive Index of a Prism Shaped Material.

FIG. 7 shows a Prism Shaped Material mounted in a FIG. 3 type (θ)-(θ) system which it is applied in a present invention method of determining the Refractive Index thereof.

Figure 8A:
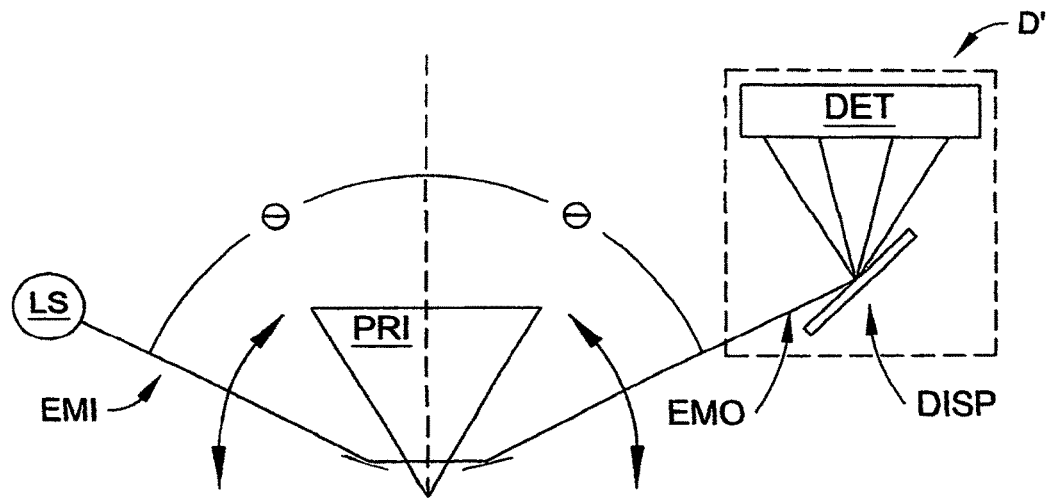
FIGS. 8A and 8B show a system for practicing a very beneficial simultaneous multiple wavelength method of the present invention.
Figure 8B:
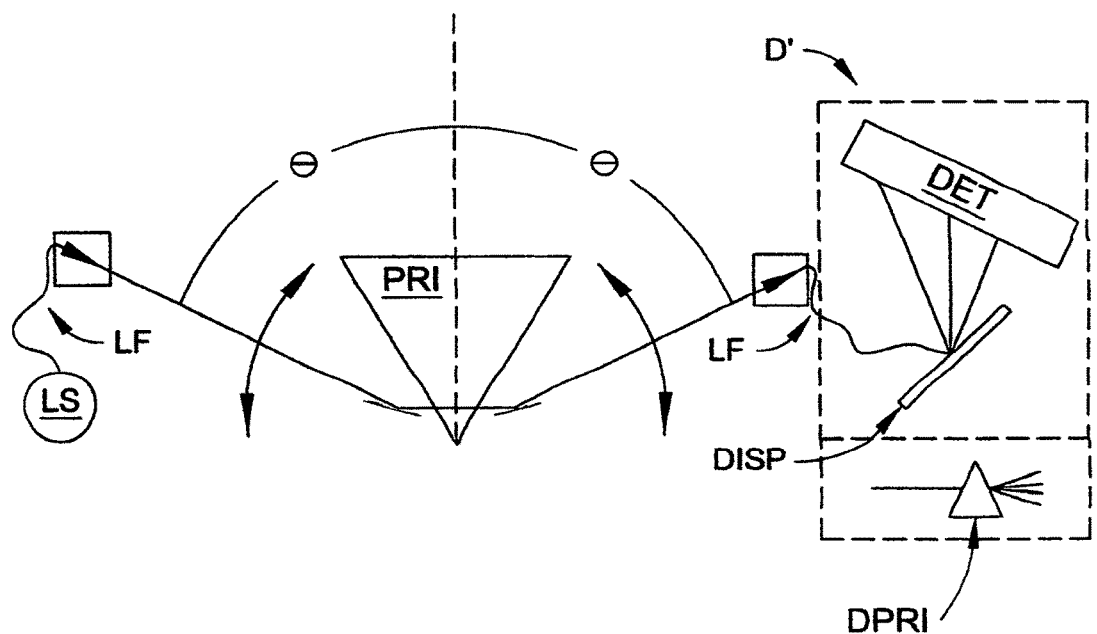
Figure 9:
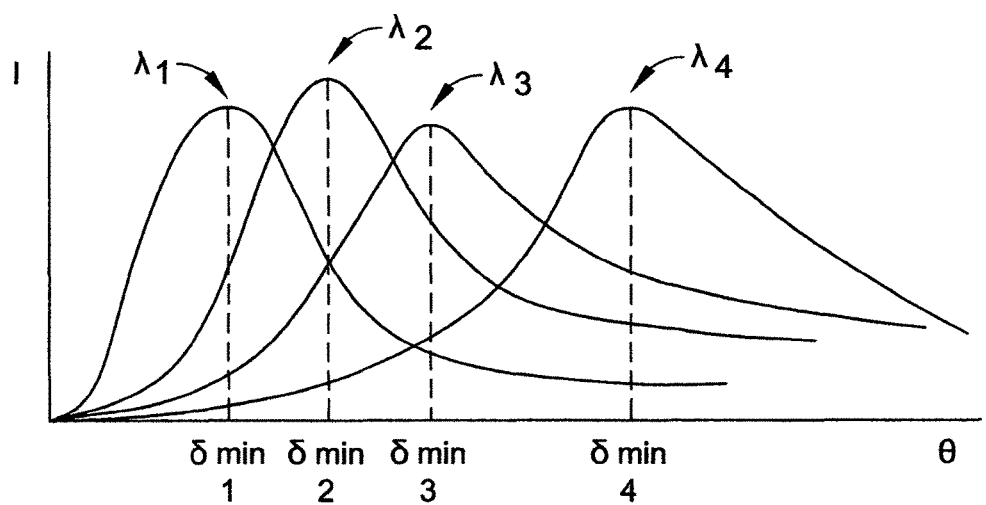
FIG. 9 plot is developed either actually or in a computer memory for multiple wavelengths.

FIGS. 8A and 8B show a system for practicing a very beneficial method of the present invention. Shown are a source (LS) of a spectroscopic beam of electromagnetic radiation, a Prism shaped material, a Disperser (DISP) and a Detector (DET) that form a unit. (D'). In use (LS) and (D'), and therefore the beams (EMI) and (EMO) are scanned through equal Theta (θ) angles, but one clockwise and the other counterclockwise, while a FIG. 9 plot is developed either actually or in a computer memory. Note that for each wavelength a different minimum deviation peak intensity is identified. That is, in one scan through a range of Theta (θ) angles can provide Refractive Indicies for a multiplicity of wavelengths. This is much faster than is typically possible in traditional known approaches and, again, utilizes a (θ)-(θ) goniometer system. The speed of data acquisition is a very important aspect enabled by of the present invention methodology. Also indicated is indication that a wavelength dispersing element can be a grating (DISP) or prism (DPRI). However, any wavelength dispersing element, (eg. a prism), can be used that directs different wavelengths into different detector elements.

It is noted that FIGS. 8A and 8B should be interpreted to allow a beam director, (eg. an optical fiber (LF)) to be present at only a source or detector side, or on both source and detector sides, or on neither side as demonstrated in FIG. 3.

FIG. 9 shows a plot can be developed, either actually or in a computer memory, for multiple wavelengths.

Figure 10:
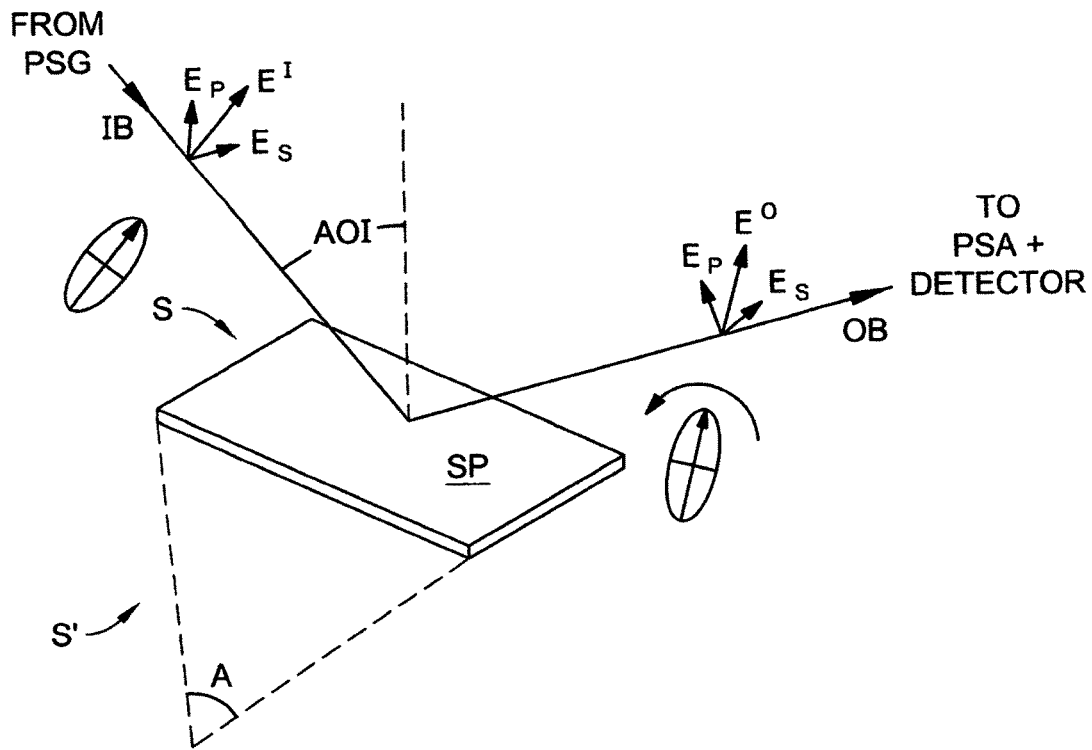
FIG. 10 shows a typical reflection mode application of ellipsometry to investigate a sample surface.

FIG. 10 shows a typical prior art reflection mode application of ellipsometry to investigate a sample surface properties (SP). (Shown in dashed lines is indication that the surface properties (SP) investigated can be on a surface of a prism). Note that a polarized beam (IB) from a polarization state generator (PSG) is directed an an Angle-of-Incidence (AOI) the the surface of the sample (S), and reflects as output beam (OB) which is directed toward a polarization state analyzer (PSA) and detector (DET). Note that polarization state ellipses are indicated for the input beam (IB) and output beam (OB). Importantly, note that the ellipse associated with the output beam (OB) is rotated, and the degree of ellipticity can be changed by interaction with the the sample (S), as comparred to that indicated for the input beam (OB). This is at least partially the result of interaction with sample (S) surface properties (SP).

Figure 11:
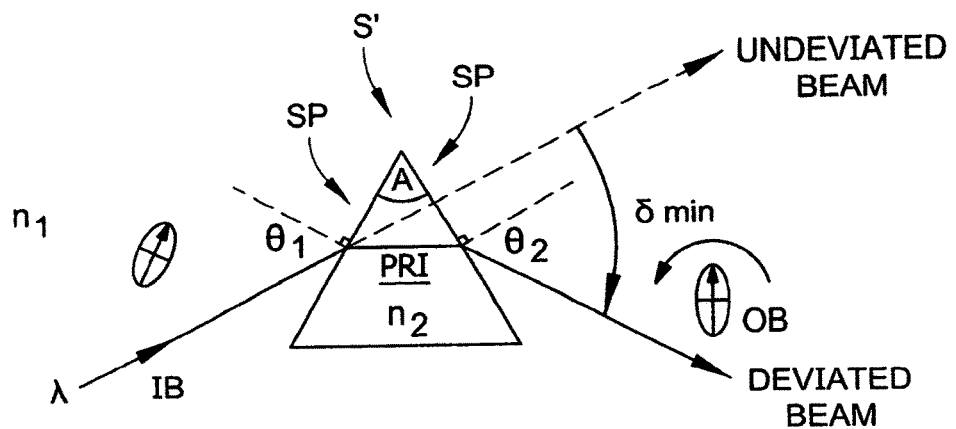
FIG. 11 is FIG. 6 drawn to further include indication of surface properties on sides thereof into which a beam enters and exits.

FIG. 11 is FIG. 6 herein, redrawn to further include indication of surface properties (SP) on sides thereof into which an input beam (IB) enters and an output beam (OB) exits. It is to be understood that when the minimum deviation condition is met by properly orienting the FIG. 11 prism (PRI) with respect to the input beam (IB), the situation of FIG. 11 is mathematically similar to that in FIG. 10, in the sense that a change in polarization state of the output beam (OB) as compared to that of the input beam (IB) provides information about the properties of surface(s) of the prism (PRI) on sides thereof where the input beam (IB) enters thereinto, and output beam (OB) exists therefrom. It is the focus of the present invention to allow not only determining bulk the refractive index and extinction coefficient by a minimum deviation procedure, as described elsewhere in this Specification, but to also determine surface properties (SP) of a prism (S') without the necessity of practicing a FIG. 10 scenario. It should be especially appreciated that unpolarized electromagnetic radiation is generally used to determine the refractive index and extinction coefficient by the minimum deviation procedure. This is because said unpolarized electromagnetic radiation is not sensitive to the indicated surface properties (SP). This is not to say, however, that a polarized beam could not be used in achieving a minimum deviation condition. In fact, it is known to use "p" and/or "s" polarized electromagnetic radiation in a minimum deviation scenario, when a prism shaped sample is known to be birefringent. However, once the Minimum Deviation condition is met using the unpolarized, (or polarized), electromagnetic radiation, proceeding to then apply Polarized electromagnetic radiation, without re-orienting the Prism (PRI) to a FIG. 10 configuration, enables much more convenient investigation of prism surface properties (SP). It should be especially appreciated that Prior Art procedure has required removing the prism (PRI) from the FIG. 11 system required to achieve the Minimum Deviation condition, (and thereat allow determination of the refractive index and extinction coefficient), and then re-configuring the prism (PRI) as shown in FIG. 10 to determine surface properties thereof, at surface(s) thereof whereat the beam of electromagnetic radiation interacts therewith. And, this might include doing so for both surfaces of the prism in the FIG. 10 system. The present invention then, allows determination of not only refractive index and extinction coefficient of a bulk Prism (PRI) shaped material using unpolarized electromagnetic radiation, but quickly, without reconfiguring the prism (PRI) as shown in FIG. 10, determine surface properties thereof by using polarized electromagnetic radiation. (That is, a FIG. 10 scenario is achieved in FIG. 11, as indicated in FIG. 10 with dashed lines. It is noted that two surfaces are included in the FIG. 11 scenario, as opposed to only one in a FIG. 10 scenario, however, this serves only to increase the sensitivity of a polarized beam to said surface properties). The convenience afforded by the present invention procedure provides utility to practitioners.

It is noted in general that surface properties can include coatings and/or roughness etc.

Figure 12:
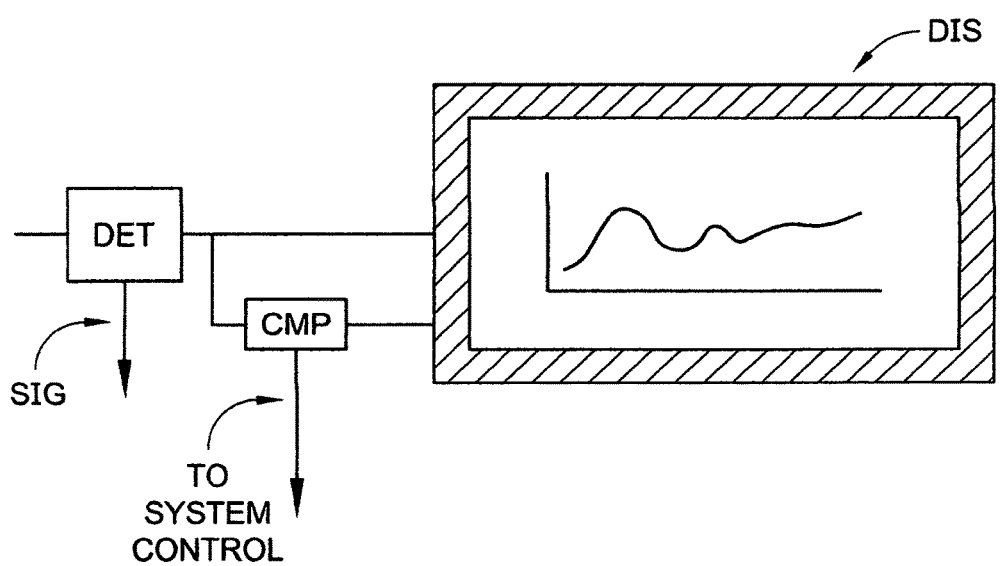
FIG. 12 is included to show a detector of an output beam (OB) can include a computer (CM) and DIsplay (DIS).

FIG. 12 is included to show a detector of an output beam (OB) can include a computer (CM) and Display (DIS).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of determining the refractive index of a prism shaped material at a given wavelength, comprising the steps a, b, c, d, e, and f, said steps a, b, c, d, e, and f being:

a) providing a system comprising:
  a1) a stage for supporting said prism shaped material,
  a2) a source of a beam of electromagnetic radiation:
    mounted directly on a rotatable support arm on a source side of said prism shaped material; or
    mounted other than on a rotatable support arm on a source side of said prism shaped material and also providing a beam directing beam director attached to said support arm on a source side of said prism shaped material;
  and positioning a detector of a beam of electromagnetic radiation:
    mounted directly on a separate rotatable support arm on a detector side of said prism shaped material, or
    mounted other than on a rotatable support arm on a detector side of said prism shaped material and also providing a beam directing beam director attached to said rotatable support arm on a detector side of said prism shaped material;
  each of said sample and detector side rotatable supports being rotatable about a common axis so as to enable directing a beam of electromagnetic radiation provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward and enters said detector of beam of electromagnetic radiation;
  a3) a computer;
b) mounting a prism shaped material to said stage, said prism shaped material having converging source and detector sides that form an apex angle "A" where they intersect;
c) while causing said source of a beam of electromagnetic radiation to provide a beam of electromagnetic radiation, rotating said rotatable support arm on said source side of said prism shaped material clockwise or counterclockwise some number of degrees to direct a beam of electromagnetic radiation toward the source side of said prism shaped material at an angle of incidence to said source side thereof, and rotating said separate rotatable support arm on said detector side of said prism shaped material counterclockwise or clockwise respectively, to the same magnitude number of degrees as was the rotatable support arm to which the source is attached and monitoring the intensity of the beam entering said detector as a result;
d) repeating step c) for multiplicity of additional input beam angles of incidence and monitoring the intensity of the beam entering said detector as a result for each said angle to determine the optimum angle of incidence of said electromagnetic beam with respect to said source side of said prism shaped material at which the detector indicates a maximum intensity; and
e) for the optimum maximum intensity angle of incidence determined in step d), in said computer, applying the following formula:

$$n2 = \frac{(\sin((A + (180 - 2(\theta) \text{ optimum angle}))/2))}{\sin(A/2)} n1$$

to determine n2,
where n1 and n2 are the refractive indicies of the ambient environment surrounding said prism shaped material, and of said prism shaped material, respectively, and f) said method further comprising adapting the source provided in step a2), or providing a different source of electromagnetic radiation to serve as an ellipsometer system source of a beam of electromagnetic radiation, then causing a beam provided thereby to pass through a polarization state generator, follow a substantially similar path as did the source of a beam of electromagnetic radiation provided in step a2) through said prism material oriented as in step e), pass through a polarization state analyzer and enter the same detector as also provided in step a2), or a different detector of electromagnetic radiation, which same or different detector serves as said ellipsometer system detector, followed by acquiring ellipsometric data from said detector and applying it to characterize surface properties of said prism.

2. A method as in claim 1, wherein the source of a beam of electromagnetic radiation is directly attached to the said rotatable support arm on said source side of said prism shaped material, and wherein the beam diffractor and detector of electromagnetic radiation exiting said prism shaped material is directly attached to said rotatable support arm on said detector side of said prism shaped material.

3. A method as in claim 1, wherein the source of a beam of electromagnetic radiation provides a beam that is directed to the prism shaped material by a beam director that is attached to the said support arm on said source side of said prism shaped material, and/or wherein the beam of electromagnetic radiation exiting said prism shaped material is directed to the beam diffractor and detector by a beam director that is attached to said support arm on said detector side of said prism shaped material.

4. A method as in claim 1, wherein the step of adjusting each of the source side and detector sides rotatable support arms through equal angles, involves a mechanism that adjusts each of the source and detector side rotatable support arms independently.

5. A method as in claim 1, wherein the step of providing adjusting each of the source side and detector sides rotatable support arms through equal angles, involves use of a theta ($\theta$)-theta ($\theta$) mechanism wherein adjusting the source side rotatable support arm, automatically results in said detector side rotatable support arm being adjusted.

6. A method as in claim 1, in which the prism shaped material has an empty volume therein and into which is caused to be present a liquid, the optical constants of which are to be determined.

7. A method as in claim 1, in which the source of electromagnetic radiation is spectroscopic and wherein said method is repeated a plurality of times, for a plurality of wavelengths, to determine refractive index at each thereof.

8. A method as in claim 1, which further comprises determining the extinction coefficient of said prism shaped material, by:

g) changing the position of said stage so that the electromagnetic beam passing therethrough passes through a different length of said prism shaped material, and monitoring the output of said detector of a beam of electromagnetic radiation to provide the intensity exiting said prism shaped material; and h) applying said intensity value obtained in step g, and the intensity value previously obtained in step c, and relating them to path lengths of said beam as it passes through said prism shaped material, to determine the extinction coefficient.

9. A method as in claim 1, in which the common axis about which the rotatable source side support and detector side support arms rotate is oriented substantially horizontally, or substantially vertically in lab coordinates.

10. A method as in claim 1 wherein the prism shaped material is of a known refractive index, and wherein its measured value is used to calibrate the system so that it reads accurately as well as repeatably.

11. A method as in claim 1, in which all method steps are carried out under control of a computer and/or the method includes storing at least some output provided by the detector in non-transitory machine readable media, and analyzing at least some output provided by the detector.

* * * * *